US00PP10551P

United States Patent [19]

Osiecki

[11] Patent Number: Plant 10,551

[45] Date of Patent: Aug. 11, 1998

[54] ANTHURIUM PLANT 'A8'

[75] Inventor: Marian W. Osiecki, Marianna, Fla.

[73] Assignee: Oglesby Plants International, Inc., Altha, Fla.

[21] Appl. No.: 850,517

[22] Filed: May 2, 1997

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz

[57] ABSTRACT

A new and distinct cultivar of Anthurium is provided. It is a medium size plant, suitable for production in 12.5 cm to 20 cm pots from a single tissue culture produced microcutting 'A8' has very vigorous growth; early and abundant branching; full and symmetrical growth habit; early, abundant year-round flowering. Prominent, bright red, highly glossy spathes, typical from the onset of flowering, are held above and among leaves on strong peduncles and remain on the plant for several months past maturity. Relatively light spadixes contrast with the spathes.

2 Drawing Sheets

SUMMARY OF THE INVENTION

This invention relates to a new and distinct Anthurium cultivar characterized by the following combination of repeatedly observed traits:

1. Medium size,
2. full plant,
3. vigorous growth,
4. early and abundant branching,
5. early, abundant and year-round flowering,
6. Inflorescences typical from the onset of flowering,
7. bright red, highly glossy spathes contrasting with relatively light spadixes;

and primary selected for those characteristics being so selected from the progeny of the cross stated below grown near Altha, Fla. in a cultivated area.

ORIGIN AN ASEXUAL REPRODUCTION

The new cultivar is a product of a planned breeding program carried out at Oglesby Plant Laboratories, Inc., near Altha, Fla. The female parent was a selected seeding of *Anthurium andreanum* designed "AR 44" and the male parent was a selected clone of Anthurium 'Ruth Morat'. The cross was made in 1991, the seedling was selected in 1993, and it has since been reproduced by tissue culture in the vicinity of Altha, Fla. with the characteristics stated, found to be maintained through successive generations.

This new cultivar has been identified as Anthurium 'A8'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'A8' was approximately 15 months from planting a single tissue cultured microcutting and was grown in a 12.5 cm pot.

In the photographs:

DETAILED DESCRIPTION OF THE NEW CULTIVAR

Figure 1:
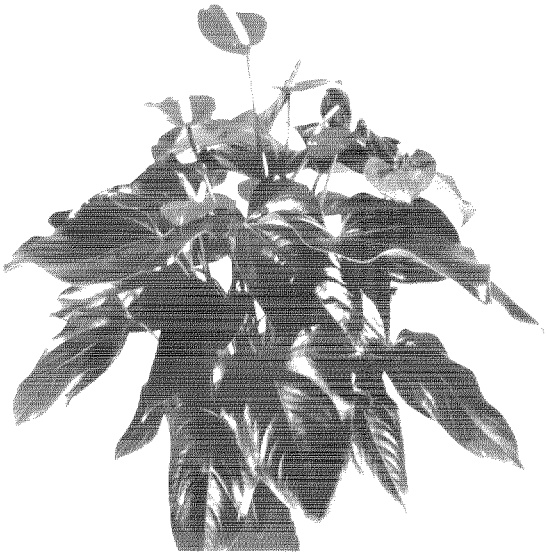
FIG. 1 depicts the whole plant.
Figure 2:
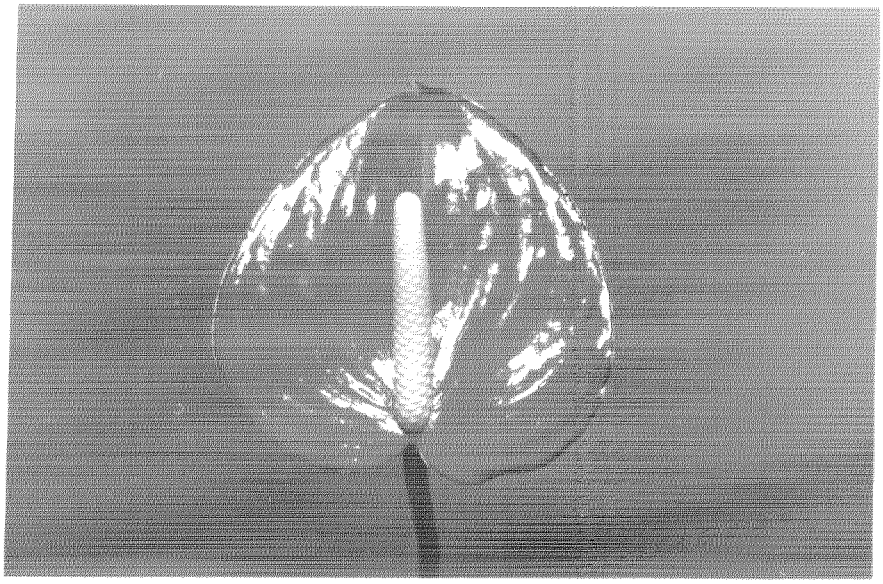
FIG. 2 illustrates the mature inflorescence.
Figure 3:
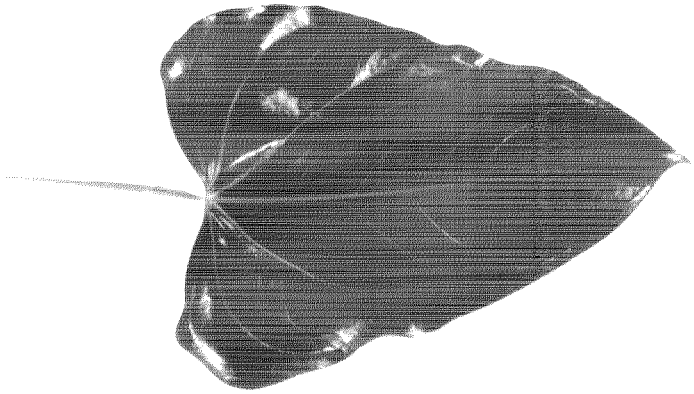
FIG. 3 illustrates a top of a mature leaf.
Figure 4:
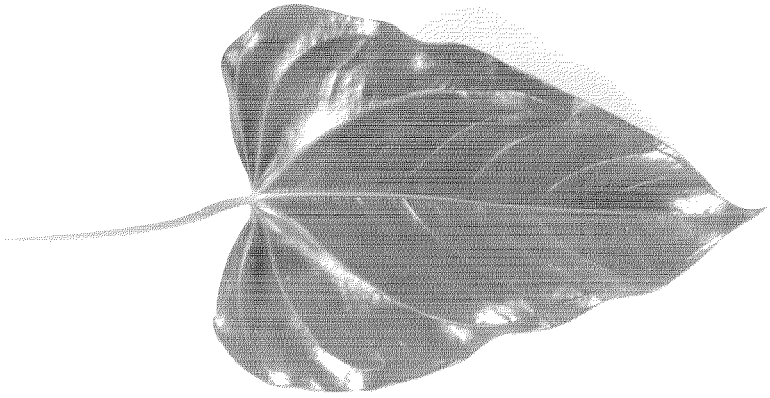
FIG. 4 illustrates the bottom of a mature leaf.

The following observations and measurements describe plants grown near Altha, Fla. under greenhouse conditions. These observations and measurements were recorded in May and June 1996 from mature plants (about 13–14 months from planting tissue cultured microcuttings) grown in 12.5 cm pots. Fully developed organs on the main stem were used for measurements and color description, unless otherwise indicated. Color values were determined on May 13, 1996 under natural, indirect light of approximately 600–1300 foot-candles. Color references are made to The R.H.S. Color Chart, except where general color terms of ordinary significance are used.

'A8' has not been observed under all possible environmental conditions. The phenotype may vary with variations in environment and horticultural practices, such as temperature, light intensity, day length, fertilization and propagation procedure, without any change in genotype.

Parentage:

*Female parent.*—Selected seedling of *Anthurium andreanum* designated "AR 44".

*Male parent.*—Selected clone of Anthurium 'Ruth Morat'.

Propagation: Plant tissue culture.

Plant descriptions:

*Growth habit.*—Well branched, full plant, especially at the base, symmetrical.

*Height.*—Foliage 29–36 cm; with spathes 37–44 cm.

*Width.*—51–63 cm.

Petiole:

*Size.*—18.7–22.4 cm long, 4.0–4.8 mm in diameter immediately below geniculum.

*Geniculum.*—2.6–3.1 cm long, 5.3–5.7 mm in diameter at the base.

*Petiole wings.*—3.0–3.7 cm long, not conspicuous.

*Color.*—Geniculum: Front: 146 A (yellow-green), except for an approximately 1 mm wide, often red-brown, shallow, longitundinal groove in the center of geniculum. Groove coloration gradually changes to that of surrounding geniculum. Back: 144 A (yellow-green). Below geniculum: Front: 146 A-B with some 144 A (both yellow-green). Back: 144 A (yellow-green); base darker than 144 A with some 137 C (green). Petiole wings: 146 A-B with some 144 A (both yellow-green).

Leaf blade:

*Position.*—Midrib of most leaf blades is horizontal or down from horizontal.

*Shape.*—Ovate, usually slightly asymmetric; tip acuminate, often curled; base cordate. Leaves produced at early stage of plant development have more truncate or obtuse bases. The proximal part of the blade on each side of the midrib often slightly curves upward. Margin wavy, entire.

*Size.*—21.5–25.2 cm long; 14.1–16.0 cm wide; length to width ratio 1.5–1.7:1.

*Texture.*—Thick, smooth, glossy; young leaves polished.

*Veins.*—Prominent near the base, less conspicuous near the tip.

*Color.*—Newly unrolled: Adaxial: lighter and more yellow 147 A, darker and more green than 146 A (both yellow-green). Veins: proximal more than half of midrib and proximal sections of the two adjacent primary veins lighter than the surrounding tissue (between 146 B and 144 A — yellow-green). Abaxial: 146 A-B (yellow-green). Veins: proximal more than half of midrib between 146 C and 144 A-B (yellow-green). Other primary veins similar to or slightly lighter in color than the surrounding tissue. Mature Leaf: Adaxial: Much darker than 147 A (yellow-green). Veins: proximal more that half of midrib and proximal sections of the two adjacent primary veins 146 A-B (yellow-green). Abaxial: 146 A and 147 B (both yellow-green). Veins: midrib 144 A-B except for the distal portion; proximal sections of other primary veins between 146 B-C and 144 A (all yellow-green).

Scale leaves:

*Covering lateral bud penultimate to mature inflorescence.*—Length: 8.5–12.0 cm; rolled longitudinally. Color: Abaxial: 144 A (yellow-green).

*Between peduncle and main stem.*—Length: 3.5–5.0 cm. Color: Abaxial: Two elevated ribs 144 B (yellow-green). Area between and beside ribs lighter (144 D, 145 B yellow-green) and a little translucent. Tip and narrow edges of the ribs and of the scale leaf sometimes partially brown.

Inflorescence:

*Arrangement.*—Spathes above and between leaves on strong peduncles. Spadix low on the spathe. Ratio spathe length to spadix length 1.6–18.1.

*Development.*—In a closed bud midrib is usually approximately 30°–60° above horizontal. When spathe unrolls pistils start protruding from the proximal approximately ⅓ of spadix and spathe quickly becomes reflexed. At inflorescence maturity, proximal spathe midrib usually approximates horizontal positions, spadix usually forms an angle with spathe midrib of approximately 50°–70° and pistils are visible on approximately ¾ of the spadix.

Peduncle:

*Size.*—29–33 cm long; 3.8–4.5 mm in diameter immediately below spathe.

*Stipe.*—Very short (not measurable).

*Color.*—Front: 144 A with some 146 A-B, especially in the proximal part (both yellow-green). Back: 144 A (yellow-green) distally; proximal more than half is darker than 144 A.

Spathe:

*Shape.*—Wide ovate; first spathes more deltoid. At inflorescence maturity, spathes almost flat; rarely the lobes slightly curve frontwards. Lobes extend 0.8–1.4 cm past peduncle. Sometimes margin slightly wavy. In the distal half spathe margin often slightly curves backwards except for the tip. Tip cuspidate with aristate tendencies, margin rolling frontwards; base cordate, sometimes slightly asymmetric;

*Size (flattened).*—7.3–9.1 cm long, 6.5–8.2 cm wide; length to width ratio 1.0–1.1.

*Texture.*—Thick, very glossy; young spathes highly polished. Very slight puckering in the proximal half; the surface of the distal half almost flat. Small raised areas are scattered in an irregular pattern on the front side, especially in the proximal half.

*Color.*—Closed bud: 51 A, 53 C-D (both red).

*Newly unrolled spathe.*—Up to 1 mm wide stripe along the margin on both sides of spathe is darker than remainder of the spathe — between 53 A (red) and 187 A (greyed-purple). Front: Between 46 A and 45 A (both red). Back: similar to 53 B-C with some resemblance to 47 A and sometimes to 45 D (all red).

*Mature inflorescence.*—Up to 1 mm wide stripe along the margin on both sides of spathe is darker than remainder of the spathe — similar to 53 A (red) with some resemblance to 187 A (greyed-purple). Front: 45 A or sometimes a little darker (red). Back: mixture of 47 A, 51 A, 45 D (all red).

Spadix:

*Shape.*—Columnar, slightly tapering in the distal section.

*Size.*—4.2–5.5 cm long, 7.0–8.6 mm in diameter (with the pistils).

*Color.*—Young inflorescence with newly unrolled spathe: Proximal ⅓–½, where pistils start protruding, 51 D, 50 D and 54 D (all red) with some 50 C and 51 C at base and top of this zone; it merges with 34 D (orange-red) of the distal zone. Mature inflorescence: Proximal zone, with developed pistils, between 36 D and 49 D (both red) at the base; distally becoming slightly darker with some 56 A-B (red) and eventualy blending with a short zone, composed of 51 C, D, 54 C, D, and 50 C, D (all red), in which pistils start protruding. The most distal zone comprises orange-red (34 C, 35 B) and red (37 A, 38 A, 39 B, 41 C, 42 D, 44 D) colors. After all pistils have developed distinct color zones are no longer present — a mixture of 36 D and 49 D at the proximal end gradually merges with a mixture of 51 D and 56 A (all red) at the distal end.

Botanical flower:

*Perianth.*—Very well visible between pistils, segments united.

*Pistil.*—Small, similar in color to perianth; stigmas minute.

*Stamens.*—Not visible before pollen release.

Flowering: Flowers naturally in 12.5 cm pots, about 10–11 months from planting tissue cultured microcuttings. Continuous year-round flowering. At approximately 13 months four to seven inflorescences visible above and among leaves.

Spathe longevity: Spathe retains red color for approximately three to four weeks following appearance of bud above or among leaves and then gradually turns green. It remains on the plant enhancing its ornamental value for up to seven months.

Roots: Roots developed above soil line are thick, fleshy and non-branching. Young roots are red or red-brown except for yellow-green distal zone. Older roots or root segments are grey or grey-brown. Numerous roots developed below soil line are thick, fleshy, cream in color with yellow root caps.

Disease and insect resistance: No unusual susceptibility to diseases or insects noted to date.

Comparison with the known cultivars:

The new cultivar can be compared to the known cultivar 'Ruth Morat' U.S. Plant Pat. No. 8,540 a/k/a 'Lady Ruth' and '75-10' U.S. Plant Pat. No. 9,355 a/k/a 'Red Hot' (as shown in table 1). The comparisons were made on plants grown under similar conditions in a greenhouse near Altha, Fla.

'A8' is distinguished from both cultivars by its more vigorous growth; earlier flowering; more prominent, larger, brighter red, glossier spathes with greater longevity; lighter spadixes that contrast stronger with the spathes and larger leaf blades.

'A8' is further distinguished from '75-10' by a better quality inflorescences at the beginning of flowering; lower position of spathes on the plant; fuller growth habit; green peduncles and petioles; lighter color of newly unrolled leaf blades and less upright spathes.

'A8' is further distinguished from 'Ruth Morat' by its more abundant flowering; stronger peduncles; cordate leaf blade bases.

TABLE 1

Comparison of Anthurium 'A8' with the cultivars 'Ruth Morat' and '75–10'.

| | 'A8' | 'Ruth Morat' | '75–10' |
|---|---|---|---|
| leaf blade length (cm) | 21.5–25.2 | 20.9–23.3 | 19.0–20.1 |
| leaf blade width (cm) | 14.1–16.0 | 10.6–11.5 | 10.2–11.5 |
| spathe length (cm) | 7.3–9.1 | 6.3–6.8 | 3.3–5.2 |
| spathe width (cm) | 6.5–8.2 | 5.2–5.9 | 3.5–5.0 |
| #inflorescences at 10.5 months | 2–3* | 0 | 0–1** |
| #inflorescences at 13 months | 4–7 | 3–4 | 3–6 |

*good quality
**deformed

I claim:

1. A new and distinct cultivar of Anthurium plant named 'A8', substantially as described and illustrated herein, characterized particularly as to novelty by its vigorous growth; early and abundant branching; symmetrical growth habit; early, abundant year-round flowering; inflorescence typical from the onset of flowering; prominent, bright red, glossy, long lived spathes held on strong peduncles above and among leaves and relatively light spadixes contrasting with the spathes.

* * * * *

UNITED STATES PATENT AND TRADEMARK OFFICE

CERTIFICATE OF CORRECTION

PATENT NO. : PP 10,551
DATED : August 11, 1998
INVENTOR(S) : Marian W. Osiecki

It is certified that error appears in the above-identified patent and that said Letters Patent is hereby corrected as shown below:

Column 2,
Line 8, delete "cultured" and insert -- culture produced --;
Line 39, delete "not conspicuous" and insert -- inconspicuous --;

Column 3,
Line 31, after "Abaxial: " insert -- Between --;
Line 49, delete "1.6-18.1." and insert -- 1.6-1.8:1. --;
Line 56, delete "positions" and insert -- position --;

Column 4,
Line 3, after "spathes" insert -- usually --;
Line 12, delete "1.0-1.1." and insert -- 1.0-1.1:1. --;
Line 60, delete "cultured" and insert -- culture produced --;
Line 65, delete "weeks" and insert -- months --;

Signed and Sealed this

Fifth Day of March, 2002

*Attest:*

*Attesting Officer*

JAMES E. ROGAN
*Director of the United States Patent and Trademark Office*